United States Patent [19]
Nikoonahad et al.

[11] Patent Number: 5,530,550
[45] Date of Patent: Jun. 25, 1996

[54] OPTICAL WAFER POSITIONING SYSTEM

[75] Inventors: Mehrdad Nikoonahad, Menlo Park; Philip R. Rigg, Saratoga; Keith B. Wells, Santa Cruz; David S. Calhoun, Mountain View, all of Calif.

[73] Assignee: Tencor Instruments, Mountain View, Calif.

[21] Appl. No.: 361,131

[22] Filed: Dec. 21, 1994

[51] Int. Cl.$^6$ ..................................................... G01B 11/14
[52] U.S. Cl. ...................................... 356/375; 250/559.31
[58] Field of Search .................................... 356/373, 375, 356/376, 381; 250/559.27, 559.38, 559.31

[56] References Cited

U.S. PATENT DOCUMENTS

| | | | |
|---|---|---|---|
| 4,589,773 | 5/1986 | Ido et al. | 356/376 |
| 4,748,333 | 5/1988 | Mizutani et al. | 250/561 |
| 4,786,815 | 11/1988 | Walker et al. | 250/559.38 |
| 4,864,123 | 9/1989 | Mizutani et al. | 250/225 |
| 4,864,147 | 9/1989 | Ikari et al. | 250/559.38 |
| 4,936,676 | 6/1990 | Stauffer | 356/375 |
| 5,004,929 | 4/1991 | Kakinoki et al. | 356/376 |
| 5,162,642 | 11/1992 | Akamatsu et al. | 356/376 |
| 5,166,516 | 11/1992 | Kajimura | 250/234 |
| 5,272,517 | 12/1993 | Tokura | 356/375 |

*Primary Examiner*—F. L. Evans
*Attorney, Agent, or Firm*—Majestic, Parsons, Siebert & Hsue

[57] ABSTRACT

The position detector has a sensitivity characteristic graded along a direction transverse to the surface, so that the output of the position detector is used to determine a height of the surface. A surface height detection and positioning device for use in a surface inspection system. An incident beam of light impinges obliquely upon the surface, and a position detector is disposed to receive specularly reflected light, producing a plurality of electrical signals, with a mechanical window, defining an aperture, placed in front of the detector. The aperture's width, along the scan direction, is of sufficient size so as to create a train of signals from each of the plurality of electrical signals, having a frequency equal to the scan frequency. These electrical signals carry information responsive to both the position of reflected beam impinging on the detector and the beam's intensity and are, in turn, related to a height of the surface. To abrogate information responsive to intensity variations at the position sensitive detector, an electronic circuit is employed which determines the sum and the difference of the plurality of signals relating to wafer height and beam intensity, producing a summed signal and a difference signal respectively. The difference signal is then divided by the summed signal, thereby producing a normalized signal which represents the height of the wafer surface without regards to these reflected beam intensity variations. These signals are synchronized to the scan frequency which facilitates removing unwanted signals resulting from thermal drifts and ambient light.

39 Claims, 6 Drawing Sheets

OPTICAL WAFER POSITIONING SYSTEM

TECHNICAL FIELD

The present invention relates to a system for aligning a wafer or the like. In particular, the system facilitates optical detection of flaws and particles on a surface of a semiconductor wafer.

BACKGROUND ART

During the production of semiconductor wafers for integrated circuits (ICs), optical scanning for defects or contaminants on a surface of the wafers is common. Such scanning can involve focusing a beam of light to a spot on the surface and detecting whether the light is scattered, as opposed to being specularly reflected from that spot, thereby signaling the presence of anomalies, i.e., particulate contaminants or pattern defects, at that spot. It is often useful to inspect wafer surfaces for anomalies at various stages during such production.

It is known that particle to background signal contrast can be optimized by directing the beam obliquely at the wafer surface. Each time a wafer is scanned, it is important that the surface is accurately positioned, in order that the scanning beam is focused on the surface and to ascertain the position on the surface of any particles or defects. This is especially true for detecting anomalies using periodic feature comparison where a slight change in height or tilt of the wafer surface can lead to meaningless results, because periodic feature comparison requires near perfect registration.

In U.S. Pat. No. 5,272,517, Tokura teaches a height measurement apparatus in which a laser light beam is directed normally toward a surface to reflect from an inclined feature, such as a solder flow, connecting an IC with a printed circuit board (PCB). Recognizing that the surface provided reflected light with varying intensity which altered the height measurements, Tokura vibrated a position of the laser light beam, relative to the surface. The light reflected from the surface is collected at a detector and temporally averaged into a mean height while the position of the laser light is vibrated. The mean height is determined to be the final height calculated.

U.S. Pat. No. 5,166,516 to Kajimura teaches a slant detection and control mechanism for a scanning probe microscope in which a light beam is reflected off a back surface of a cantilevered beam having a probe on a front surface. The reflected beam undergoes multiple reflections to arrive at a detector that determines the deflection of the probe toward an object being scanned.

In U.S. Pat. No. 4,748,333, Mizutani et al. teach a surface displacement sensor having multiple slits and lenses aligned along a trajectory of light reflecting from the surface at an oblique angle, and a sensor positioned at an end of that trajectory which receives increased light when the slits are aligned with the light. The multiple slits are provided to overcome inaccuracies in the height measurements due to differing thin film thicknesses which varies the intensity of the reflected light. At least one of the slits can be narrowed for increasing the accuracy of the surface displacement.

U.S. Pat. No. 4,864,123 to Mizutani et al. also utilizes the alignment of multiple slits and lenses along a trajectory of light that is obliquely reflected off a surface to determine the level of that surface. This patent teaches the advantage of polarization correcting optics for adjusting the intensity ratio between orthogonal polarized components of the reflected light.

It is an object of the present invention to devise an accurate measurement of surface height for a wafer inspection system without being adversely influenced by variations of intensity of reflected light.

It is another object of the present invention that the measurement of the surface height is accomplished without regard to the height variations due to patterned features on the surface.

It is another object of the present invention to measure surface height using the same source of light that is used for particle inspection of the system.

It is yet another object of the present system to provide means for using the measurement of the surface height to adjust a position of the surface during particle inspection.

SUMMARY OF THE INVENTION

The above objects are accomplished by having a position sensitive detector disposed in a path of a beam reflected from a spot scanned along a scan line over a surface at a scan frequency, with the detector positioned near an image plane of the surface formed by a focusing assembly. The detector has a light sensitivity graded along a first direction of the image plane with the image of the spot varying, in the first direction, with the height of the surface. The detector produces a plurality of electrical signals representing uncorrected position information of the image of the spot. A mechanical window, defining an aperture, is placed in front of the detector. The aperture's width, across which the image of the spot is scanned, allows only the central portion of the light of the image of a scan line to impinge on the detector. As a result, the plurality of signals are transmitted as synchronized pulses having a frequency equal to the scan frequency. An electronic circuit is employed to receive the synchronized signals which removes any information responsive to intensity variations of the reflected beam. These intensity variations are often attributed to material forming patterns on the surface, as well as interference effects due to local height changes. Locking the signals to the scan frequency facilitates removing information responsive to thermal drifts in the system's electronics and optics which manifest as dc signals.

To remove information responsive to intensity variations, the electronic circuit determines the sum and the difference of the plurality of signals relating to wafer height and beam intensity, producing a summed signal and a difference signal respectively. The difference signal is then divided by the summed signal, thereby producing a normalized signal which represents the height of the wafer surface without regards to reflected beam intensity variations. Also, a spatial filter is employed at a Fourier transform plane of the system to remove all but the zero order diffraction of the reflected light. In this manner, the higher order diffractions do not impinge upon the detector, thereby abrogating height ambiguity.

The incident beam of light impinges upon a wafer surface, typically at a large angle measured from the normal to the surface, and reflects from the surface at a similar angle. Focussing lenses are positioned in the path of the reflected beam, focusing it at an image plane, where the waist of the reflected beam is imaged onto a light sensitive position detector. A deflector is placed in the path of the beam to scan it along a line on the surface. A plurality of electrical signals are produced from the position sensitive detector which carry information concerning both the position of reflected beam impinging on the detector and the beam's intensity, which is a function of the wafer's reflectivity. These electrical signals are, in turn, related to a height of the surface.

The scanning of the wafer surface for anomalies may be accomplished with a beam of light that is directed onto the surface of a predefined angle and is deflected along a first horizontal direction, defined as the y-axis, by an acousto-optic deflector (AOD) or a mechanical device such as a resonant or polygon scanner. With any of these devices, each scan period corresponds to a scan of the surface along the y-axis direction. A servo controlled positioning system moves the wafer surface along a second horizontal direction, perpendicular to the y-axis and defined as the x-axis, as the beam scans in the y-axis, such that many scans along the y-axis are performed during a single sweep of the wafer surface in the x-axis. During each scan along the y-axis, information about the effective height of the wafer surface is collected by the position sensitive detector so that a vertical position, defined as the z-axis, of the wafer surface can be measured and dynamically adjusted on-the-fly.

The wafer alignment system can augment an existing particle detection system that scans a wafer surface with obliquely incident light to detect scattered light by utilizing the specularly reflected beam which would otherwise be sent to a beam dump. In such a system, the incident beam scans across the surface in a series of lines that are generally normal to the incident beam. The image of the waist of the reflected beam can be used to determine the alignment of the wafer surface by employing a position sensitive detector with a sensitivity graded in one direction, perpendicular with respect to the scan direction. Other types of position detectors having a graded sensitivity may alternatively be employed. For example, if it is desired to detect surface tilt, as well as surface height, a position sensitive detector having a bi-directional sensitivity may be employed. The bi-directional position sensitive detector would have a sensitivity graded onto it parallel to the direction of the scan line, and another perpendicular to it. With this structure, the position sensitive detector produces a plurality of electrical signals relating to wafer height and tilt or the position of the beam along a scan line.

BEST MODE FOR CARRYING OUT THE INVENTION

Figure 1:
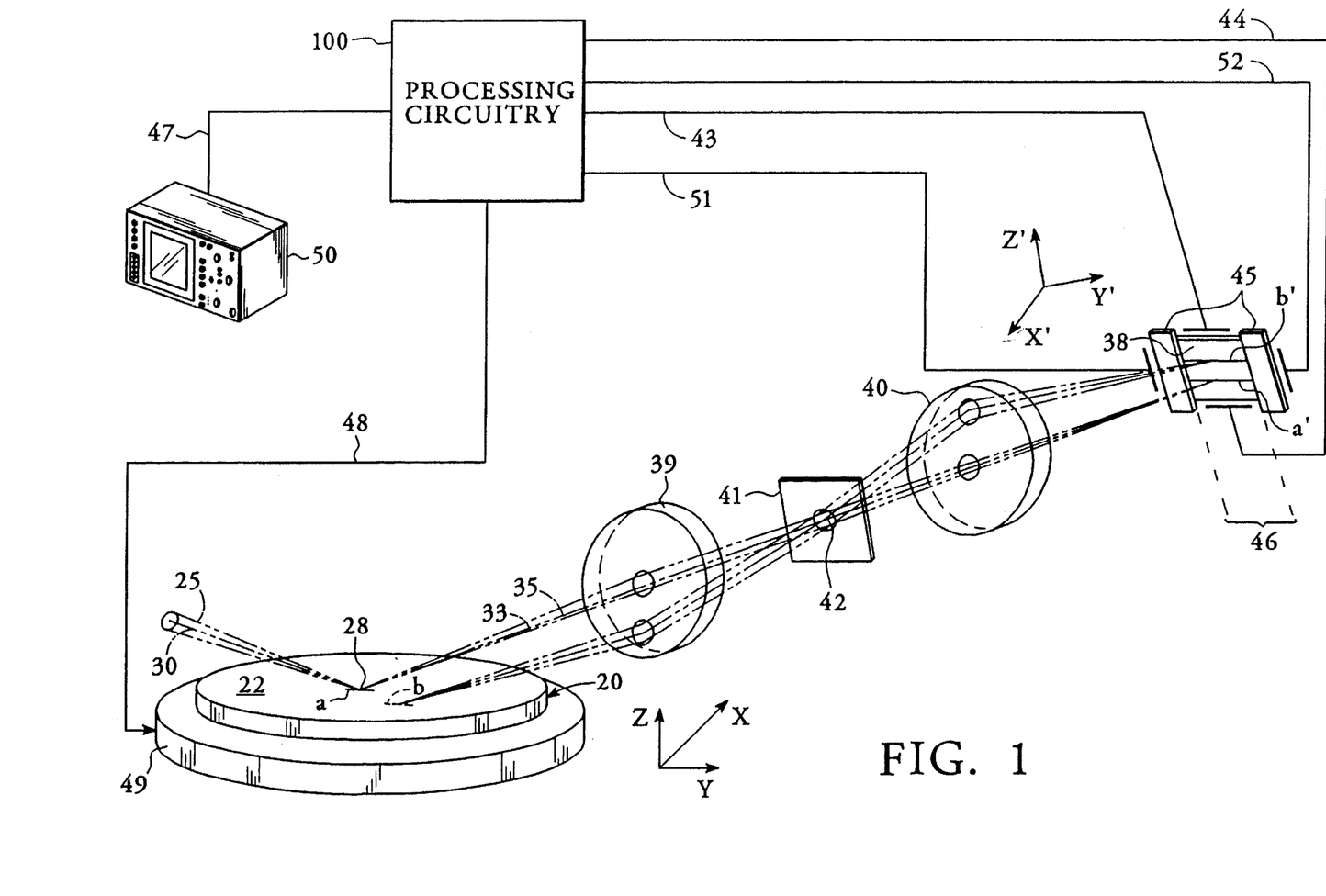
FIG. 1 is a diagram of a surface positioning system of the present invention for particle detection on a surface.

FIG. 1 shows a wafer 20 having a surface 22 with an obliquely incident beam of light 25 being focused on a spot 28 on the surface 22. The incident beam 25, which may be produced by a laser, is centered about an axis 30 that is preferably in a range of between 55° and 85° from normal to the wafer surface. The incident beam 25 is primarily reflected from the spot 28 as a reflected beam 33 centered about an axis 35 oriented generally at an equal and opposite angle from normal to the wafer surface as the incident beam axis 30. While searching for anomalies on the surface 22, the incident beam 25 repeatedly scans portions of the surface, such as line (a), which represents one such small scan line, a center of which coincides with spot 28. Scan line (a) may have a length of about 3 mm to about 30 mm in the length, depending upon the application desired.

The reflected beam 33 diverges from a focused "waist" at the spot 28 that may range from less than 1 μm to 100 μm, depending upon the application. The divergence of the reflected beam 33 may be due to both a defocusing of the incident beam 25 beyond the waist and due to some roughness of the surface 22 that causes imperfect reflection. A telescope is placed in the path of the reflected beam 33 to image the waist of the reflected beam 33 onto a position sensitive detector 38, located near an image plane of the spot 28 and scan line (a). The telescope includes pair of focusing lenses 39 and 40, and a spatial filter 41. The telescope may have unity magnification, or a higher magnification in order to increase the sensitivity of the detector to measuring variations in wafer height, discussed more fully below. The spatial filter 41 is positioned at the Fourier transform plane of the system, to remove higher order diffraction patterns generally caused by a patterned surface 22, while allowing specularly reflected or zero order diffracted light to pass through essentially unperturbed.

The lens 40 focuses the parallel rays of the beam 33 that pass through the spatial filter 41 onto the position sensitive detector 38 located a distance f on the opposite side of the second lens 40 from the filter 41. Thus, an image (a') of the scan line (a) is present on the detector 38. Each lens 39 and 40 is formed from thin achromatic lenses, sandwiched together, having different indices of refraction selected to remove aberrations in the lenses.

The position sensitive detector 38 is positioned in the image plane, parallel to the Z' axis, which forms an angle θ with respect to the optical axis, defined by lens 40. Angle θ is generally in the range of 5° to 35° and is dependent upon the angle of incidence of the beam 25, with respect to the wafer surface, so that angle θ and the angle of incidence are complementary, i.e., the sum of these two angles is 90. At the spatial filter 41, the beam is stationary and only swings around a pivot point 42. As the wafer 20 moves along in the Z direction, the image of the spot 28 moves correspondingly in the Z' direction on the position sensitive detector 38.

Figure 2:
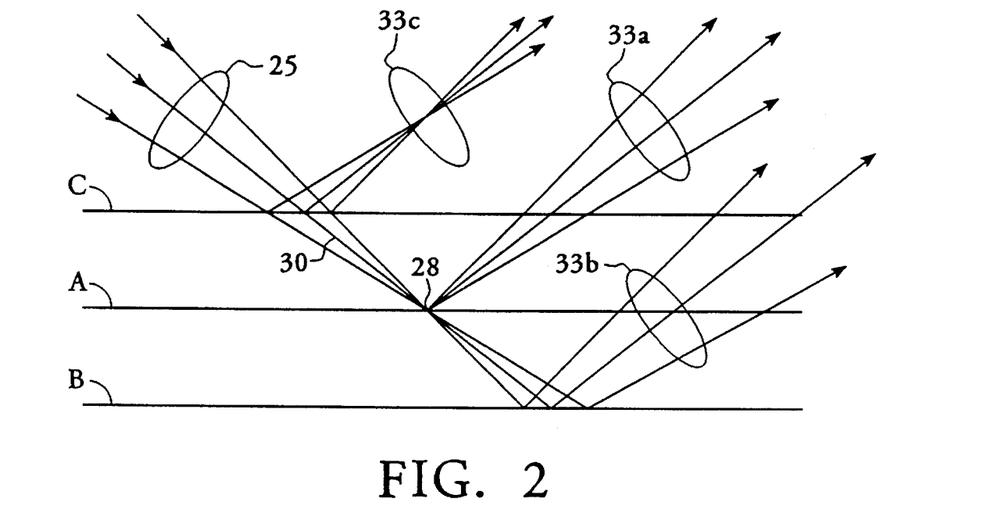
FIG. 2 is a side view of a beam reflecting from a surface at various height positions in accord with the present invention.

Referring also to FIG. 2, the Z'-to-Z correspondence is dependent upon the magnification provided by lenses 39 and 40 and defined as follows:

$$\Delta Z' = -2M^2 \Delta Z_w$$

where $\Delta Z_w$ is the change in position of the wafer surface 22 along the Z axis, $\Delta Z'$ is the change in position of a corresponding image position on detector 38 and M is the magnification. A two-to-one correspondence may be obtained using unity magnification so that a one micron shift in the height of the wafer in a Z direction results in a two micron shift in the image position on the position sensitive detector in the opposite Z direction. For example, when the surface 22 is at nominal position A, an image of the waist of the beam 33a reflected along scan line (a) is shown as line (a') on the position sensitive detector 38. Scan line (b) is shown on the surface 22 when the wafer height has moved to a lower Z height B, with respect to the nominal position A of the surface 22. As a result, a reflected beam 33b diverges and the image of the waist of the beam reflected along scan line (b), (b'), is positioned on the position sensitive detector 38, above scan line (a'). If the wafer moves to a higher Z position C with respect to the nominal position A, a converging reflected beam 33c has its waist images on the detector below scan line (a'), as (c'). A more sensitive Z'-to-Z correspondence may be obtained using higher magnification. If lenses 39 and 40 provided 2X magnification, a one micron shift in the surface height along the Z direction would correspond to an 8 micron shift on the detector along the Z' axis, in the opposite direction.

The position sensitive detector is a silicon device. It is doped with a graded concentration of dopants so that the signals out of each lead 43 and 44 is proportional to both the position and the intensity of the image on the detector 38. A mechanical window 45 is placed in the path of the reflected beam between the surface 22 and the detector 38. The mechanical window 45 defines an aperture 46, resulting in only the central portion of the light of the image of a scan line impinging on the detector 38. In response to that portion of the light impinging upon the detector 38, an electrical signal is transmitted, having a width equal to the length of time required for the image line to travel the width of the aperture 46. The width of the aperture 46, along the direction of scan line (a') and perpendicular to both the X' and Z' directions, is of sufficient size so as to create a train of signals on leads 43 and 44, synchronized with the scan frequency.

Processing circuitry 100 receives these signals and determines the actual height of the wafer as a result of image position, without regard to the intensity of the beam impinging on the detector 38. Synchronizing the signals with the scan frequency increases the accuracy of the height measurement by attenuating unwanted signals that may result, for example, from thermal drifts in either the electronic circuitry or optical components and ambient light. The processing circuitry 100 produces a normalized signal that may be transmitted along lead line 47 to an open loop response, e.g., to obtain a visual map of the surface 20 height variation. Alternatively, a normalized signal may be sent along lead 48 to a servo controlled stage 49 that will position the wafer 20 in the Z direction so that the surface 22 is in a preferred position.

Other types of position sensitive detectors may alternatively be employed. For example, although not necessary for merely determining wafer height, a bi-directional detector may be employed to detect surface tilt, as well as surface height. This detector would have dopants graded in a direction perpendicular to the Z' direction and would include two additional leads 51 and 52. Similar to the signals sent on leads 43 and 44, the signals on leads 51 and 52 would be proportional to both the image position and intensity. The signals on leads 51 and 52, however, correspond to the spot 28 position along a scan line (a), whereas the signals on leads 43 and 44 corresponds to the wafer height. By comparing these signals, the variation of the surface height can be determined along the scan line, thereby providing information concerning the tilt of the wafer surface.

Figure 3:
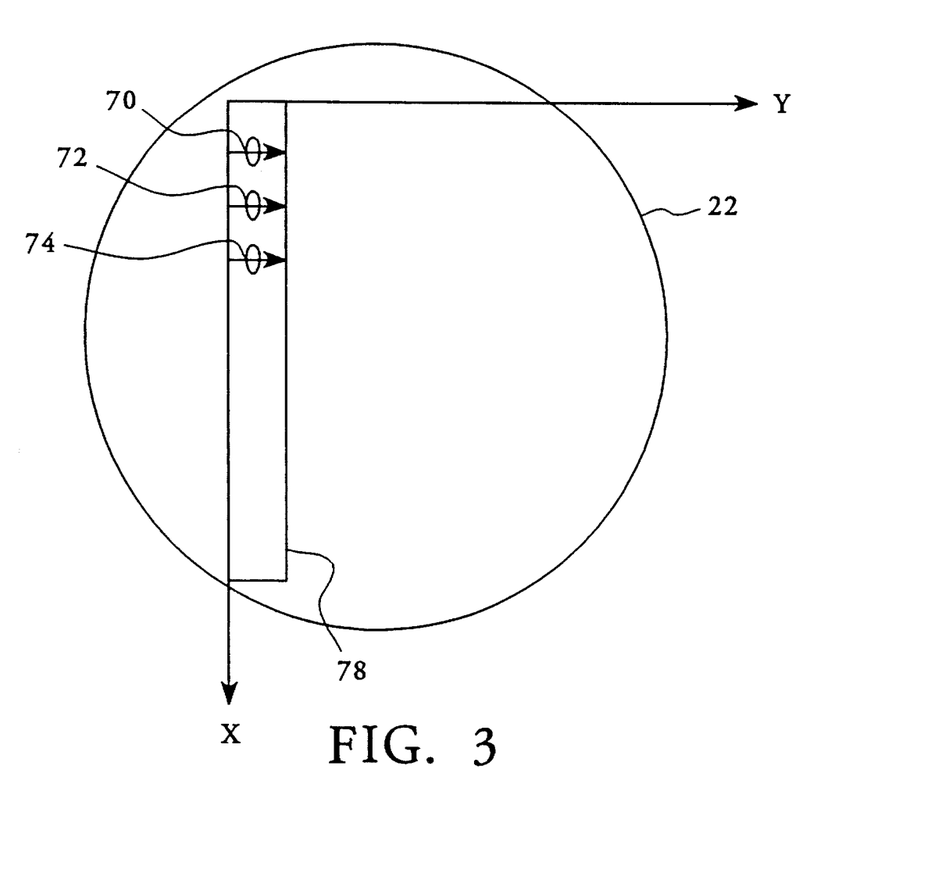
FIG. 3 is a top view of a scanning sequence on the surface of FIG. 1.

FIG. 3 shows a top view of the scanning of a wafer surface 22 by an incident beam, not shown, that is oriented generally along the X and Z directions, the Z direction pointing out of the plane of the paper. The beam scans across the wafer surface along the Y direction in individual scan lines 70, 72 and 74 that have a length that is a fraction of a diameter of that wafer 20. The scanning may be produced by an AOD or mechanical device over a wide range of frequencies, from less than 100 Hz to nearly 100 kHz. Faster or slower scanning frequencies may be employed, depending upon a tradeoff between particle sensitivity and wafer throughput. As the beam scans back and forth in the Y direction, the wafer is moved along the X direction by the stage 49, which is not shown in this figure. Although the scan lines 70, 72 and 74 are shown spaced apart for ease of illustration, actual scan lines would be much closer together. After the wafer surface 22 has been moved along the X direction so that the scan lines have swept across a strip 78 having a width equal to the length of the scan lines and a length spanning the surface along the X direction, the wafer surface 22 is moved a distance in the Y direction approximately equal to the length of a scan line, and a similar strip adjoining strip 78 is scanned. In this fashion the entire surface 22 is scanned with the beam.

Referring to both FIGS. 1 and 3, the reflected image of a scan line 72 is received by the position detector 38, which sends an electrical signal to the signal processing circuitry 100. The processing circuitry 100 causes the stage 49 to raise or lower the wafer surface 22 for a subsequent scan 74. In addition, if a bi-directional position sensitive detector were employed, processing circuitry 100 could cause stage 49 to rotate in order to compensate for any tilt measured in the surface 22 along scan line 72. Thus, the system of FIGS. 1 and 2 automatically positions a wafer surface 22 at a preferred height while the surface 22 is being scanned.

Figure 4:
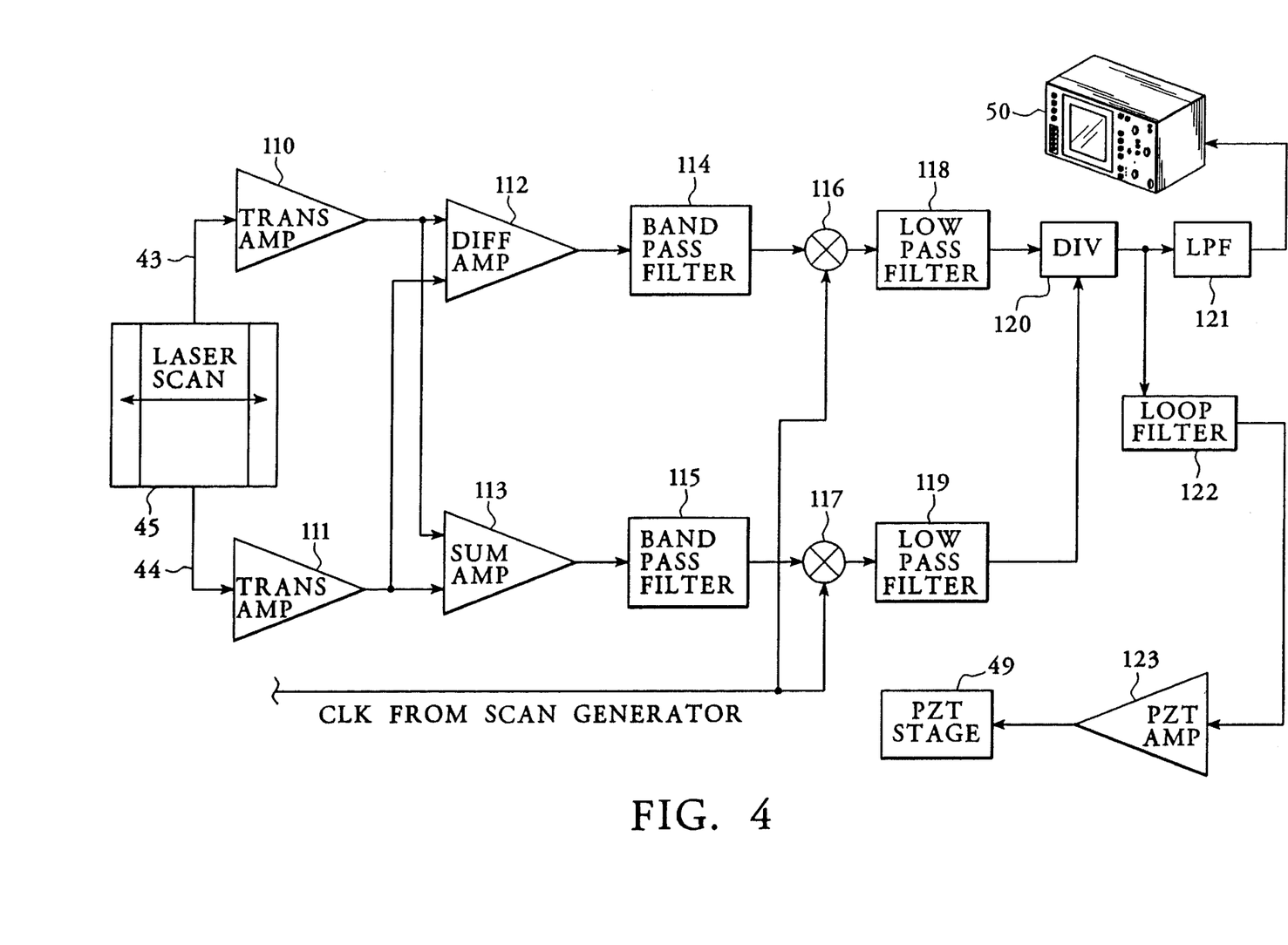
FIG. 4 is a block diagram of the processing circuitry shown in FIG. 1.

FIG. 4 offers an expanded view of the electronics involved in the processing circuitry 100. In the preferred embodiment, current signals are present on each of the leads 43 and 44. Each current signal represents uncorrected position information of the image on the detector 38 and can be described as follows:

$$S_1(t)=PR(t)R_\lambda G(0.5+z_s/L)$$

$$S_2(t)=PR(t)R_\lambda G(0.5-z_s/L)$$

where P is the incident power on the wafer in watts, R is the reflectivity, $R_\lambda$ is the responsivity of the sensor in Amperes/watt, G is the gain of the transimpedance amplifier in Ohms, $z_s$ is the distance on the sensor measured in microns, and L is the length of the position sensitive detector in the image plane, along the Z' direction.

Each lead 43 and 44 is connected to a transimpedance amplifier 110 and 111, each of which converts the respective current signal into a voltage signal. The output of each transimpedance amplifier 110 and 111 is electrically coupled to a difference amplifier 112 and a summing amplifier 113. The difference amplifier obtains the difference between the voltage signal received from transimpedance amplifier 110 and the voltage signal received from transimpedance amplifier 111, forming a difference signal. The summing amplifier 113 adds the voltage signal received from transimpedance amplifier 110 with the voltage signal received from transimpedance amplifier 111, forming a summed signal.

The output of the difference amplifier 112 is electrically coupled to a first band pass filter 114, and the output of the summing amplifier 113 is electrically coupled to a second band pass filter 115. The first and second band pass filters 114 and 115 remove unwanted noise from the summed and difference signals by attenuating signals not having a frequency that corresponds to a range of predetermined frequencies, centered about the scan frequency. In the preferred embodiment, filters 114 and 115 pass a 100 kHz bandwidth. Electrically coupled to receive the output of the first band pass filter 114 is a first multiplying circuit 116, and electrically coupled to the second band pass filter 115 is a second multiplying circuit 117.

The circuits 116 and 117 multiply the signals received from the band pass filters 114 and 115 by a square wave clock signal, derived from the scan generator, and operate so as to down-convert to baseband, both the signals from the band pass filters 114 and 115, which are at the scan frequency, and harmonics. This facilitate removing unwanted signals corresponding to thermal drifts and ambient light. In order to select only the baseband signals from the outputs of the multiplying circuits 116 and 117, these circuits are each electrically coupled to a first and second low pass filter 118 and 119, respectively. The first and second low pass filters have narrow bandwidths of only a few Hz. The narrow bandwidth results in the outputs of filters 118 and 119 having signals originating from a few Hz on either side of the fundamental and harmonics of the scan frequency, with all other frequencies being attenuated. Both the first and the second low pass filters 118 and 119 are electrically coupled to a divider circuit 120.

The divider circuit 120 divides the difference signal with the summed signal, producing a normalized signal. The normalized signal represents the position of the line on the position sensitive detector, without regard to the line intensity or variation of line intensity across the scan. In this manner, the height of the wafer 20 can be determined without errors caused by intensity variations of the reflective beam due to, inter alia, pattern features on the surface 22. The normalized signal may be applied depending upon the application. In one embodiment, the normalized signal is filtered by a third low pass filter 121 coupled between the divider circuit 120 and an open loop response circuit, such as a monitor 50, where a map of height variations can be observed. Alternatively, the normalized signal can be used on a closed loop system where it is once again filtered by a loop filter 122, and electrically coupled to a piezo electric/servo stage 49 via an amplifier 123.

Figure 5:
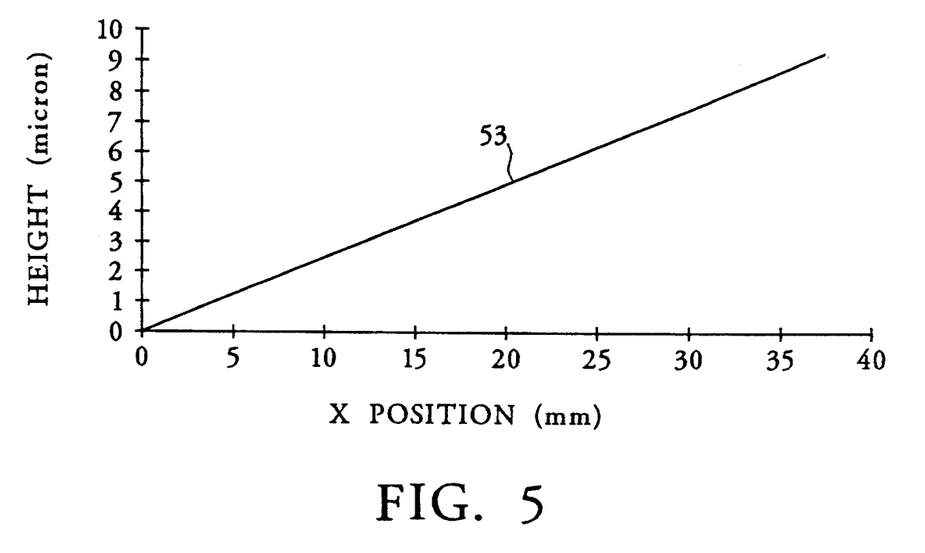
FIG. 5 is a graphical representation of height variations of a surface over the length of a 40 millimeter scan path.

FIG. 5 is a graphical representation of computer simulations carried out to determine the effects of dc offset in the electronics on the accuracy of height measurement. The abscissa X of the graph represents spatial positions of a beam along a scan path. The ordinate or vertical axis represents a simulated height of the surface. FIG. 5 shows that the height variation across a 40 millimeter scan path is approximately 10 microns.

Figure 6:
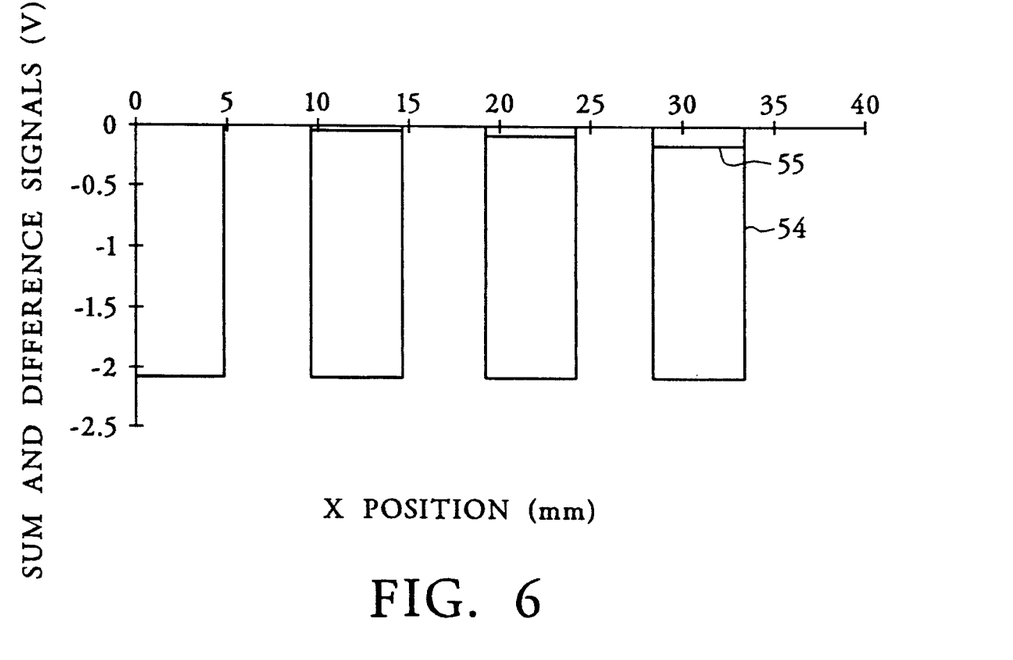
FIG. 6 is a graphical representation of electrical signal amplitude (V) versus beam scan position along the x-axis, (X), of the present invention.

FIG. 6 shows simulated voltage levels V of the summed signal 54 and the difference signal 55, produced by the summing and difference amplifiers, over the same 40 millimeter scan of the simulated scan path referred to in FIG. 5. The mechanical window, as described above, ensures that the summed and difference signals are pulses having a frequency equal to the scan frequency with a desired duty cycle. In the preferred embodiment, although not critical, the desired duty cycle is 50%.

Figure 7:
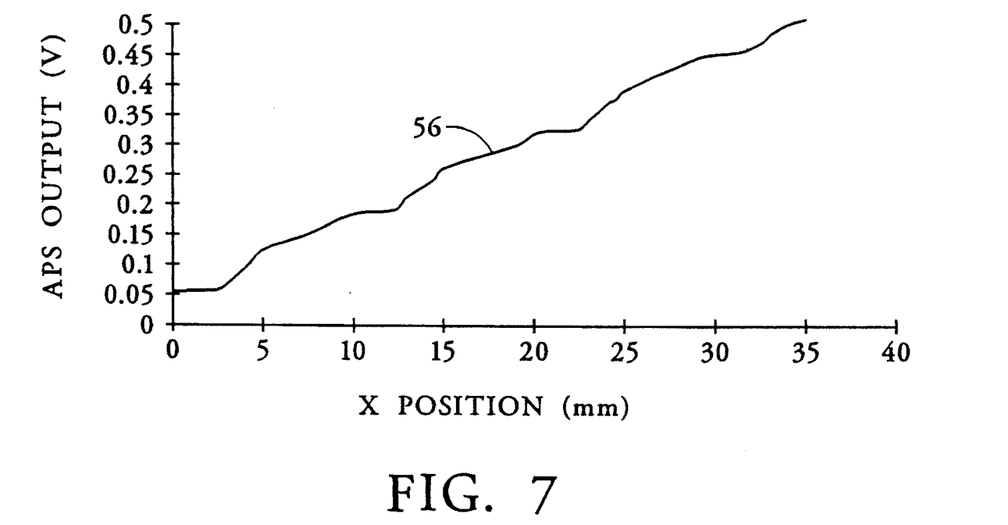
FIG. 7 is a graphical representation of an electrical signal amplitude (V) produced by the processing circuitry, shown in FIGS. 1 and 3, versus the beam scan position along the x-axis, (X), of the present invention.
Figure 8:
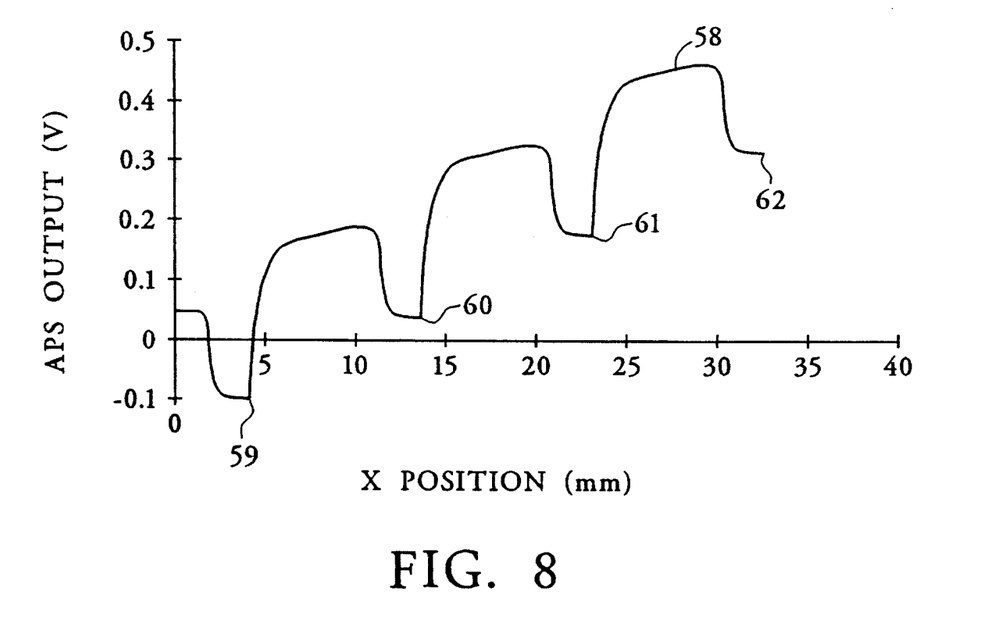
FIG. 8 is a graphical demonstration showing the effects of having an improper DC offset present on the electrical signals shown in FIG. 5.

FIG. 7 shows line 56 as a graphical representation of a simulated normalized signal, with APS voltage output V at spatial positions X of the 40 millimeter scan path referred to in FIGS. 5 and 6. For purposes of this invention, APS output is measured at monitor 50, shown in FIGS. 1 and 4. It is important to note that the slope is almost perfectly linear. The linearity of this slope is necessary to obtain the proper height adjustment of the wafer, because the stage displacement is a function of the drive voltage V and the drive voltage is derived from the voltage of the normalized signal. The linearity of line 56 results from the summed 54 and difference 55 signals having a DC offset from ground approximating 0 mV. The effect of DC offset is shown in FIG. 8, wherein line 58 is a graphical representation of a simulated normalized signal with the summed 54 and difference 55 signals having a $-100$ mv offset from ground. The non-linearity of the slope of the signals 58 is shown where peaks 59, 60, 61 and 62 dip approximately $-1.5$ V. Considering that the displacement of the stage is a function of the voltage level of the normalized signal, it can easily be understood that great error would occur in the wafer position should the offset of the summed 54 and difference 55 signals vary significantly from 0 mV.

Figure 9:
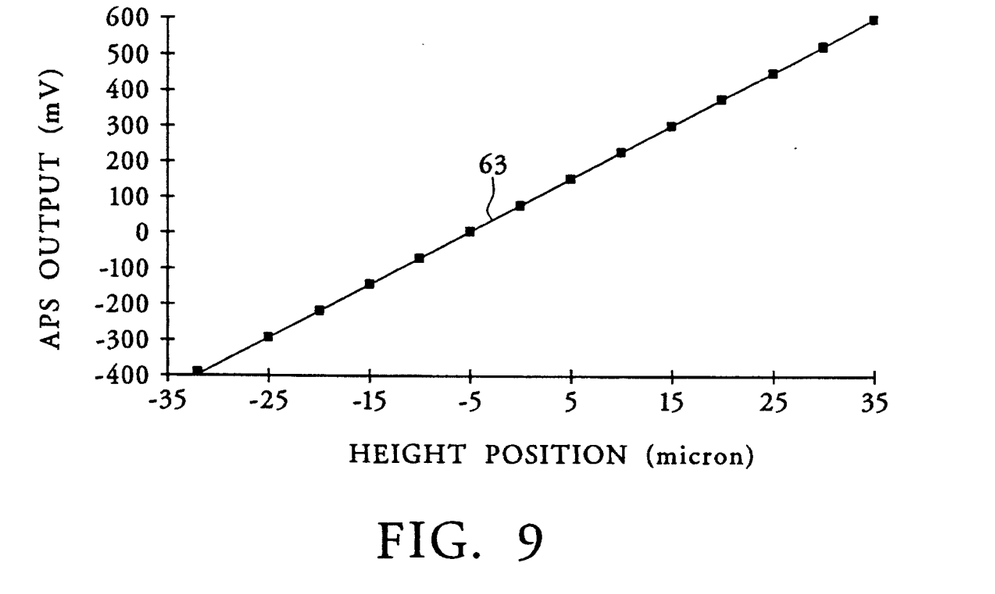
FIG. 9 is a graphical representation of an electrical signal amplitude versus the height position of the surface shown in FIG. 1 of the present invention.

The system was evaluated on a wide range of wafers both bare and patterned with FIG. 9 showing a typical result. Line 63 shows the APS output of the processing circuitry versus height position. The height position was measured by a mechanical gauge. Over a nearly 70 micron change in height, the output voltage of the system changed by one volt, with the slope of line 63 remaining linear.

Figure 10:
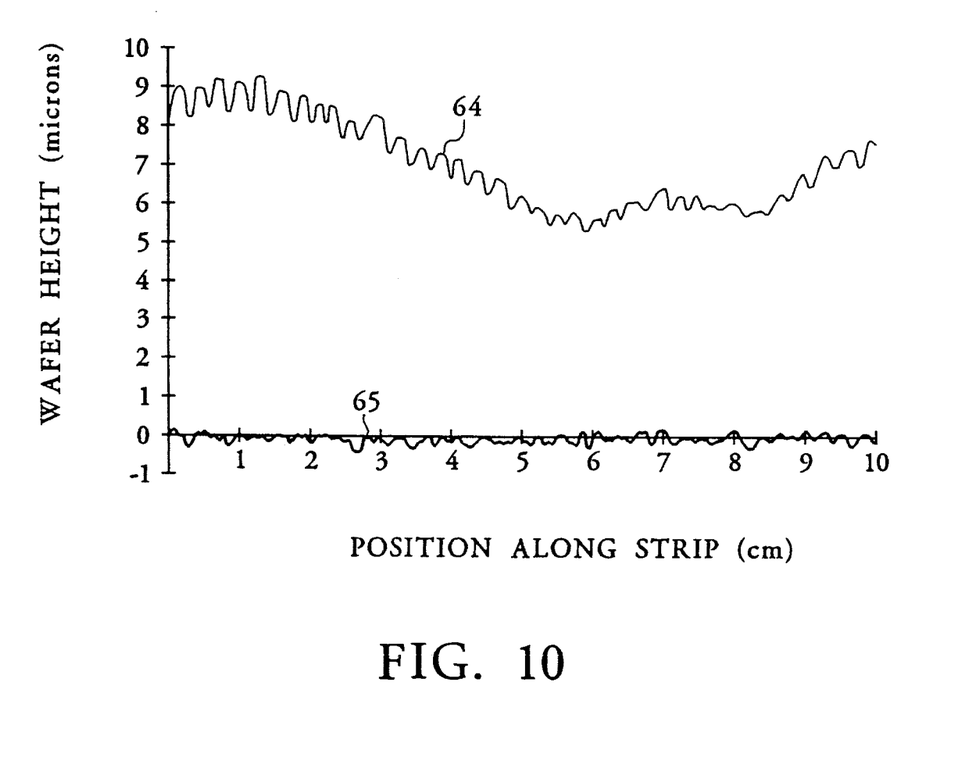
FIG. 10 is a graphic representation of wafer height along a strip of the wafer surface.

FIG. 10 demonstrates the effectiveness of the electric/servo stage in adjusting the surface, on-the-fly, to obtain an optimum height of the surface. Line 64 represents the variation in surface height along a 10 cm strip of the surface, without compensating for the variations. This is referred to as an open loop response. Over the 10 cm strip, the height of the surface varied by almost 4 microns. Line 65, on the other hand, represents the height variation along the same 10 cm strip, except, in this instance, the electric/servo stage compensates for the height variations. It is clear that the stage was able to maintain the wafer at a constant height with less than 0.5 micron of variation, as shown by line 65.

The above-described invention is particularly useful in periodic feature comparison of a patterned wafer, where scattered light detected by a particle detector depends upon both the pattern and the presence of an anomaly at a location on a surface. The presence of an anomaly can be detected by comparing a signal from a detector generated at the same location on a plurality of dies having identical patterns. For this case, it is important that the locations for which the signal is compared are identical. An error in the height of a surface on one die relative to another can subvert this comparison. Further, locking the signals produced by the detector to the scan frequency facilitates periodic feature comparison by allowing dynamically adjusting the height and tilt of the surface on the fly as the wafer is scanned, in accord with measured variations in height and tilt of the surface.

We claim:

1. A system for detecting a height of a body comprising:

a position sensitive detector disposed in a path of a beam reflected from a spot scanned along a scan line over a surface at a scan frequency, the detector being positioned near an image plane of the surface, with the detector having a light sensitivity graded along a first direction of the image plane in which a position of an image of the spot varies, in the first direction, with the height of the surface, producing a plurality of electrical signals representing uncorrected position information of the image of the spot;

means, coupled to the position sensitive detector, for synchronizing each of the plurality of electrical signals with a frequency equal to the scan frequency, thereby establishing synchronized scan signals to remove signals not representing height information; and means responsive to the synchronized scan signals for determining a measured height of the surface at the spot.

2. The system as recited in claim 1 wherein the synchronizing means includes a mechanical window defining an aperture having a width across which the image of the spot scans, in a second direction perpendicular to the first direction, wherein the width of the aperture is of sufficient size so as to provide the synchronized scan signals with a predetermined duty cycle, and a frequency equal the scan frequency.

3. The system as recited in claim 1 wherein the position sensitive detector further includes a second light sensitivity graded along a second direction perpendicular to the first direction, in which a position of an image of the spot varies in the second direction with the position of the spot along the scan line.

4. The system as recited in claim 1 wherein the plurality of signals include a first electrical signal and a second electrical signal, each of the first and second signals carrying intensity and position information of the image of the spot in the first direction, said determining means including means for correcting said first and Second signals to derive a normalized electrical signal representing the height of the surface based solely on the position of the spot on the sensor in the first direction.

5. The system as recited in claim 4 further including means, responsive to the normalized electrical signal, for moving the surface in response to variations of the spot position on the detector in the first direction.

6. The system as recited in claim 4 wherein the correcting means includes means for summing the first and second signals, producing a summed signal and means for obtaining a difference between the first and the second signals, producing a difference signal.

7. The system as recited in claim 6 wherein the correcting means includes means for dividing the summed signal or a signal derived therefrom with the difference signal or a signal derived therefrom, producing the normalized signal.

8. The system as recited in claim 7 wherein the correcting means includes means for filtering the difference signal and means for filtering the summed signal, so that signals having a frequency different from a predetermined frequency bandwidth are attenuated, said scan frequency being in the predetermined bandwidth of frequencies.

9. The system as recited in claim 7 wherein the correcting means includes means for multiplying the difference signal or a signal derived therefrom by said scan frequency to provide a first product signal and means for multiplying the summed signal or a signal derived therefrom by said scan frequency to provide a second product signal.

10. The system as recited in claim 9 wherein the correcting means includes low pass filter means for filtering the first and second product signals.

11. The system of claim 1, said determining means including means for removing components of the reflected light other than zero order diffraction.

12. The system of claim 11, said removing means including means for converting the first and second signals or signals derived therefrom to baseband of the scan frequency.

13. The system of claim 2, wherein the width of the aperture of said mechanical window is such that the window allows only a central portion of the image of the scan line to pass.

14. A system for detecting a height of a body to be optically inspected comprising:

an incident beam of light directed obliquely at a surface of the body, the incident beam being at least partly reflected at a spot on the surface as a reflected beam, means for scanning the spot along a scan line, at a scan frequency, an imaging means for focusing the reflected beam, a position sensitive detector disposed in a path of the reflected beam near an image plane of the surface formed by the imaging means, the detector having a first light sensitivity graded along a first direction of the image plane and a second light sensitivity graded along a second direction, in which a position of an image of the spot varies in the first direction with a height of the surface and varies in the second direction in accordance with the spot position along the scan line, whereby comparing the height variation with the spot position along the scan line will determine the tilt of the surface.

15. The system as recited in claim 14 wherein the position sensitive detector produces a plurality of electrical signals representing uncorrected position information of the image of the spot, including a first electrical signal and a second electrical signal, with the uncorrected position information responsive to image position and an image intensity, and further including means coupled to the position sensitive detector for synchronizing each of the plurality of electrical signals with a frequency equal to the scan frequency, thereby establishing synchronized scan signals, and means responsive to the synchronized scan signals for correcting the uncorrected position information, producing corrected position information, the corrected position information carrying information responsive to the image position only, defining a corrected electrical signal representing the height of the surface based only on the position of the spot on the sensor in the first direction.

16. The system as recited in claim 15 wherein the synchronizing means includes a mechanical window optically coupled to the detector, and placed in the path of the reflected beam between the detector and the surface, with the mechanical window defining an aperture having a width across which the image at the spot scans in the second direction, wherein the width of the aperture is of sufficient size so as to provide the synchronized scan signals with a predetermined duty cycle and a frequency equal to the scan frequency to remove signals not representing height information.

17. The system as recited in claim 15 wherein the correcting means includes means for summing the first and second signals, producing a summed signal and means for obtaining a difference between the first and the second signals, producing a difference signal.

18. The system as recited in claim 14 wherein the correcting means includes means, in electrical communication with both the summing means and the obtaining means, for dividing the summed signal or a signal derived therefrom with the difference signal or a signal derived therefrom, producing the corrected signal.

19. The system as recited in claim 18 wherein the correcting means includes first means for filtering the difference signal and second means for filtering the summed signal, so that signals having a frequency different from a predetermined frequency bandwidth are attenuated, said scan frequency being in the predetermined frequency bandwidth.

20. The system as recited in claim 19 wherein the correcting means includes first means for multiplying the difference signal to provide a first product signal and second means for multiplying the summed signal to provide a second product signal, so that the difference and summed signals are multiplied by a predetermined frequency.

21. The system as recited in claim 20 wherein the correcting means includes low pass filter means for filtering the first and second product signals.

22. The system as recited in claim 15 further including means for moving the surface in response to said corrected electrical signal representing variations of the spot position on the detector in the first direction.

23. The system of claim 14, further comprising means for rotating the surface to compensate for the tilt.

24. A method for detecting a height of a body comprising the steps of:

disposing a position sensitive detector in a path of a beam reflected from a spot scanned along a scan line over a surface at a scan frequency, so that the detector is positioned near an image plane of the surface, the detector having a light sensitivity graded along a first direction of the image plane in which a position of an image of the spot varies, in the first direction, with the height of the surface, producing a plurality of electrical signals representing uncorrected position information of the image of the spot;

synchronizing each of the plurality of electrical signals with a frequency equal to the scan frequency, thereby establishing synchronized scan signals to remove signals not representing height information; and determining from the synchronized scan signals for a measured height of the surface at the spot.

25. The method as recited in claim 24 wherein the synchronizing step includes disposing a mechanical window between the surface and the detector, said window defining an aperture having a width across which the image of the spot scans, in a second direction perpendicular to the first direction, wherein the width of the aperture is of sufficient size so as to provide the synchronized scan signals with a predetermined duty cycle, and a frequency equal the scan frequency.

26. The method of claim 25, wherein said disposing step disposes the window so that the width of the aperture of said mechanical window is such that the window allows only a central portion of the image of the scan line to pass.

27. The method as recited in claim 24 wherein the position sensitive detector further includes a second light sensitivity graded along a second direction perpendicular to the first direction, in which a position of an image of the spot varies in the second direction with the position of the spot along the scan line.

28. The method as recited in claim 24 wherein the plurality of signals include a first electrical signal and a second electrical signal, each of the first and second signals carrying intensity and position information of the image of the spot in the first direction, said determining step including step for correcting said first and second signals to derive a normalized electrical signal representing the height of the surface based solely on the position of the spot on the sensor in the first direction.

29. The method as recited in claim 28 further including moving the surface in response to the normalized electrical signal representing variations of the spot position on the detector in the first direction.

30. The method as recited in claim 28 wherein the correcting step includes summing the first and second signals, producing a summed signal and obtaining a difference between the first and the second signals, producing a difference signal.

31. The method as recited in claim 30 wherein the correcting step includes dividing the summed signal or a signal derived therefrom with the difference signal or a signal derived therefrom, producing the normalized signal.

32. The method as recited in claim 31 wherein the correcting step includes filtering the difference signal and filtering the summed signal, so that signals having a frequency different from a predetermined frequency bandwidth are attenuated, said scan frequency being in the predetermined bandwidth of frequencies.

33. The method as recited in claim 31 wherein the correcting step includes multiplying the difference signal or a signal derived therefrom by said scan frequency to provide a first product signal and multiplying the summed signal or a signal derived therefrom by said scan frequency to provide a second product signal.

34. The method as recited in claim 33 wherein the correcting step includes low pass filtering the first and second product signals.

35. The method of claim 24, said determining step including removing components of the reflected light other than zero order diffraction.

36. The method of claim 35, said removing means including converting the first and second signals or signals derived therefrom to baseband of the scan frequency.

37. A method for detecting a height of a body to be optically inspected comprising the steps of:

directing an incident beam of light obliquely at a surface of the body, the incident beam being at least partly reflected at a spot on the surface as a reflected beam, scanning the spot along a scan line, at a scan frequency, focusing the reflected beam onto an image plane, disposing a position sensitive detector in a path of the reflected beam near the image plane of the surface, the detector having a first light sensitivity graded along a first direction of the image plane and a second light sensitivity graded along a second direction, in which a position of an image of the spot varies in the first direction with a height of the surface and varies in the second direction in accordance with the spot position along the scan line, so that a comparison of the height variation with the spot position along the scan line will determine the tilt of the surface.

38. The method as recited in claim 37 wherein the position sensitive detector produces a plurality of electrical signals representing uncorrected position information of the image of the spot, including a first electrical signal and a second electrical signal, with the uncorrected position information responsive to image position and an image intensity, said method further including synchronizing each of the first and second electrical signals with a frequency equal to the scan frequency, thereby establishing synchronized scan signals, and correcting the uncorrected position information, producing corrected position information, the corrected position information carrying information responsive to the image position only, defining a corrected electrical signal representing the height of the surface based only on the position of the spot on the sensor in the first direction.

39. The method of claim 37, further comprising rotating the surface to compensate for the tilt.

* * * * *

UNITED STATES PATENT AND TRADEMARK OFFICE
CERTIFICATE OF CORRECTION

PATENT NO. : 5,530,550
DATED : June 25, 1996
INVENTOR(S) : Mehrdad Nikoonahad et al.

It is certified that error appears in the above-indentified patent and that said Letters Patent is hereby corrected as shown below:

In Column 9, line 28, in Claim 28:
  replace "means for correcting said first and Second signals to derive" with:

--means for correcting said first and second signals to derive--

In Column 10, lines 53 and 54, in Claim 18:
  replace "The system as recited in claim 14 wherein the correcting" with:

--The system as recited in claim 17 wherein the correcting--

Signed and Sealed this

Second Day of December, 1997

Attest:

BRUCE LEHMAN

Attesting Officer

Commissioner of Patents and Trademarks